United States Patent
Coulombe et al.

(10) Patent No.: US 11,471,207 B2
(45) Date of Patent: Oct. 18, 2022

(54) ASSESSING QUALITY OF OCCLUSION

(71) Applicant: Medtronic CryoCath LP, Toronto (CA)

(72) Inventors: Nicolas Coulombe, Montreal (CA); Jean-Pierre Lalonde, Candiac (CA)

(73) Assignee: Medtronic CryoCath LP, Toronto (CA)

( * ) Notice: Subject to any disclaimer, the term of this patent is extended or adjusted under 35 U.S.C. 154(b) by 211 days.

(21) Appl. No.: 16/788,910

(22) Filed: Feb. 12, 2020

(65) Prior Publication Data

US 2020/0179029 A1 Jun. 11, 2020

Related U.S. Application Data

(63) Continuation of application No. 15/934,155, filed on Mar. 23, 2018, now Pat. No. 10,595,922, which is a
(Continued)

(51) Int. Cl.
*A61B 18/00* (2006.01)
*A61B 18/02* (2006.01)
(Continued)

(52) U.S. Cl.
CPC ............ *A61B 18/02* (2013.01); *A61B 5/0538* (2013.01); *A61B 5/6847* (2013.01);
(Continued)

(58) Field of Classification Search
CPC .............................. A61B 18/02; A61B 5/0538
(Continued)

(56) References Cited

U.S. PATENT DOCUMENTS

| 4,682,596 A | 7/1987 | Bales et al. |
| 5,014,715 A | 5/1991 | Chapolini |
| (Continued) | | |

FOREIGN PATENT DOCUMENTS

| CA | 2903280 A1 | 9/2014 |
| CN | 102355856 A | 2/2012 |
| (Continued) | | |

OTHER PUBLICATIONS

Boaz Avitall, MD, Phd, FHRS et al., The characteristics of distal balloon impedance and temperature changes during Cryo ablation: Can it guide the Cryo application?, Abstract, 2015 Heart Rhythm, May 13-16, 2015, Boston, MA. Oasis, The Online Abstract Submission System.
(Continued)

*Primary Examiner* — Nicole F Lavert
(74) *Attorney, Agent, or Firm* — Michael Best & Friedrich LLP

(57) ABSTRACT

A method, system, and device for predicting lesion quality. Specifically, lesion quality may be predicted based on an assessment of pulmonary vein occlusion using injection of an impedance-modifying agent and evaluation of changes in impedance measurements recorded by an electrode located distal to an occlusion element of the treatment device used to inject the impedance-modifying agent. The quality of the occlusion may be rated based on the changes in impedance over time within the pulmonary vein. For example, the quality of the occlusion may be rated as being good, fair, or poor. This assessment may be quickly and easily communicated to an operator.

20 Claims, 14 Drawing Sheets

Related U.S. Application Data continuation of application No. 14/689,180, filed on Apr. 17, 2015, now Pat. No. 9,956,025.

(60) Provisional application No. 62/088,267, filed on Dec. 5, 2014.

(51) Int. Cl.
  *A61B 5/00* (2006.01)
  *A61B 5/0538* (2021.01)
  *G16H 50/30* (2018.01)
  *A61M 5/00* (2006.01)

(52) U.S. Cl.
  CPC .......... *A61B 5/6862* (2013.01); *A61B 5/7275* (2013.01); *A61M 5/007* (2013.01); *G16H 50/30* (2018.01); *A61B 2018/0022* (2013.01); *A61B 2018/00375* (2013.01); *A61B 2018/00577* (2013.01); *A61B 2018/00821* (2013.01); *A61B 2018/00875* (2013.01); *A61B 2018/0212* (2013.01)

(58) Field of Classification Search
  USPC .............................................................. 606/2
  See application file for complete search history.

(56) References Cited

U.S. PATENT DOCUMENTS

| | | | |
|---|---|---|---|
| 5,639,444 | A | 6/1997 | Klaveness |
| 5,991,654 | A | 11/1999 | Tumey et al. |
| 7,951,088 | B2 | 5/2011 | Korotko et al. |
| 8,295,908 | B2 | 10/2012 | Carmeli et al. |
| 2002/0151880 | A1 | 10/2002 | Lafontaine |
| 2003/0158490 | A1 | 8/2003 | Krivitski et al. |
| 2003/0216661 | A1* | 11/2003 | Davies ................ A61B 5/0538 600/547 |
| 2007/0066975 | A1 | 3/2007 | Wong et al. |
| 2009/0182318 | A1* | 7/2009 | Abboud ............... A61B 5/0538 606/21 |
| 2010/0041984 | A1 | 2/2010 | Shapland et al. |
| 2010/0130854 | A1 | 5/2010 | Shachar et al. |
| 2011/0144637 | A1 | 6/2011 | Pageard et al. |
| 2011/0152712 | A1 | 6/2011 | Cao et al. |
| 2012/0095461 | A1 | 4/2012 | Herscher et al. |
| 2014/0276709 | A1 | 9/2014 | Wittenberger et al. |
| 2014/0330262 | A1 | 11/2014 | Jannicke et al. |
| 2015/0164570 | A1 | 6/2015 | Wittenberger et al. |

FOREIGN PATENT DOCUMENTS

| | | |
|---|---|---|
| CN | 103347456 B | 11/2016 |
| CN | 103561814 B | 7/2017 |
| CN | 103547229 B | 9/2017 |
| EP | 1025805 A1 | 8/2000 |
| EP | 1107714 B1 | 2/2007 |
| WO | 9835611 A1 | 8/1998 |
| WO | 2008088579 A2 | 7/2008 |

OTHER PUBLICATIONS

Boaz Avitall, MD, Phd, FHRS et al., Distal Cryo balloon temperature sensor to assess PV occlusion: Eliminating the need for contrast and fluoroscopy, Abstract, 2015 Heart Rhythm, May 13-16, 2015, Boston, MA. Oasis, The Online Abstract Submission System.

International Search Report and Written Opinion dated Jan. 7, 2016, for corresponding International Application No. PCT/CA2015/051250; International Filing Date: Dec. 1, 2015 consisting of 9—pages.

International Search Report and Written Opinion dated Mar. 2, 2016, for corresponding International Application No. PCT/CA2015/051272; International Filing Date: Dec. 4, 2015 consisting of 10—pages.

Supplementary European Search Report dated Aug. 6, 2018, for corresponding European Application No. 15 86 5807; consisting of 5—pages.

China National Intellectual Property Administration, Notice on the First Office Action, for corresponding Application No. 201580074808.7; dated Jul. 23, 2019, 25 pages, English translation attached.

China National Intellectual Property Administration, Notice on the First Office Action and Search Report, for corresponding Application No. 201580074807.2; dated Aug. 28, 2019, 20 pages, English translation attached.

* cited by examiner

ASSESSING QUALITY OF OCCLUSION

CROSS-REFERENCE TO RELATED APPLICATION

This application is a continuation of and claims priority to U.S. patent application Ser. No. 15/934,155, filed Mar. 23, 2018, now U.S. Pat. No. 10,595,922 issued Mar. 24, 2020 and is a continuation of and claims priority to U.S. patent application Ser. No. 14/689,180, filed Apr. 17, 2015, entitled CONTRAST AGENT TO ASSESS QUALITY OF OCCLUSION THROUGH IMPEDANCE MEASUREMENT, now U.S. Pat. No. 9,956,025 issued May 1, 2018 which application is related to and claims priority to U.S. Provisional Patent Application Ser. No. 62/088,267, filed Dec. 5, 2014, entitled USE OF COLD SALINE TO REPLACE DYE IN DETERMINING CRYO BALLOON PV OCCLUSION, the entirety of both of which is incorporated herein by reference.

STATEMENT REGARDING FEDERALLY SPONSORED RESEARCH OR DEVELOPMENT n/a

FIELD OF THE INVENTION

The present Application relates to a method, system, and device for predicting lesion quality and other interventions requiring vascular occlusion. Specifically, lesion quality may be predicted based on an assessment of pulmonary vein occlusion using an injected impedance-modifying agent. This assessment may be quickly and easily communicated to an operator.

BACKGROUND OF THE INVENTION

Cardiac arrhythmia is a condition in which the heart's normal rhythm is disrupted. Certain types of cardiac arrhythmias, including ventricular tachycardia and atrial fibrillation, may be treated by ablation (for example, radiofrequency (RF) ablation, cryoablation, ultrasound ablation, laser ablation, microwave ablation, and the like), either endocardially or epicardially.

Procedures such as pulmonary vein isolation (PVI) are commonly used to treat atrial fibrillation. This procedure generally involves the use of a cryogenic device, such as a catheter, which is positioned at the ostium of a pulmonary vein (PV) such that any blood flow exiting the PV into the left atrium (LA) is completely blocked. Once in position, the cryogenic device may be activated for a sufficient duration to create a desired lesion within myocardial tissue at the PV-LA junction, such as a PV ostium. If a cryoballoon is used as the treatment element of the cryogenic device, the balloon is typically inflated using a fluid coolant, enabling the balloon to create a circumferential lesion about the ostium and/or antrum of the PV to disrupt aberrant electrical signals exiting the PV.

The success of this procedure depends largely on the quality of the lesion(s) created during the procedure. Currently known methods for evaluating lesion quality may include monitoring the temperature within the cryoballoon, but this method can be inaccurate. The success of a PVI procedure also depends on whether the cryoballoon has completely occluded the PV. For example, a complete circumferential lesion is produced only when the cryoballoon has completely occluded the PV. Incomplete occlusion allows blood to flow from the PV being treated, past the cryoballoon, and into the left atrium of the heart. This flow of warm blood may prevent the cryoballoon from reaching temperatures low enough to create permanent lesions in the target tissue, or could leave gaps of non-ablated tissue at regions where blood leaks past the balloon. The creation of reversible lesions may not be sufficient to achieve electrical isolation and, as a result, atrial fibrillation may be likely to reoccur. Additionally, even if the PV is completely occluded, suboptimal operation of the cryoablation system may result in cryoballoon temperatures that are not low enough, or not applied for a sufficient amount of time, to create permanent lesions in the target tissue.

Current methods of assessing or monitoring PV occlusion may include monitoring changes in impedance measurements of blood and tissue. Although these methods may be effective, changes in recorded impedance caused by incomplete PV occlusion may be small and could be difficult to detect when trying to quantify the importance of the blood leak around the balloon. Both blood and tissue conduct electricity well and the distinction between their respective conductivities is small.

It is therefore desirable to provide a cryoablation method, system, and device that allows for real-time and accurate assessment of PV occlusion before a PV ablation procedure based on recorded impedance measurements. It is also desirable to provide for a method, system, and device that allow for the communication of PV occlusion assessment to the operator quickly and easily.

SUMMARY OF THE INVENTION

A method, system, and device for predicting lesion quality. Specifically, lesion quality may be predicted based on an assessment of pulmonary vein occlusion using injection of an impedance-modifying agent and evaluation of changes in impedance measurements recorded by an electrode located distal to an occlusion element of the treatment device used to inject the impedance-modifying agent. The quality of the occlusion may be rated based on the changes in impedance over time within the pulmonary vein A system for assessing occlusion may include a treatment device including an occlusion element and an electrode distal to the occlusion element a console including a fluid source in fluid communication with the treatment device, the fluid being a mixture of a contrast medium and an impedance-modifying agent and a processor programmed to receive impedance values recorded by the electrode, to calculate a change in the impedance values over time, and to determine an occlusion status based on the change in the impedance data. The processor may further be programmed to predict the quality of a lesion created in tissue by the occlusion element based on the occlusion status determination. For example, a determination that the pulmonary vein is partially occluded may include at least one of assigning the occlusion by the processor a poor rating and assigning the occlusion a fair rating and a determination that the pulmonary vein is completely occluded includes assigning the occlusion by the processor a good rating. Further, occlusion may be assigned a good rating when the change in impedance values has a first value, occlusion may be assigned a fair rating when the change in impedance values has a second value, and occlusion may be assigned a poor rating when the change in impedance values has a third value, the first value being less than each of the second value and the third value. The occlusion element may be a balloon. The device may further include a thermocouple located within the balloon. The treatment device may further include a shaft having a central lumen and a distal opening, the shaft being at least partially disposed within the balloon, the central lumen and distal opening being in fluid communication with the fluid source. The mixture of the contrast medium and the impedance-modifying agent may be injected from the treatment device into a pulmonary vein. The impedance-modifying agent may increase the impedance of fluid within the pulmonary vein. For example, the processor may be programmed to determine the occlusion status is poor when the impedance values recorded by the electrode initially increase and then decrease over time and/or may be programmed to determine the occlusion status is good when the impedance values recorded by the electrode initially increase and then plateau. Alternatively, the impedance-modifying agent may decrease the impedance of fluid within the pulmonary vein. For example, the processor may be programmed to determine the occlusion status is poor when the impedance values recorded by the electrode initially decrease and then increase over time and/or may be programmed to determine the occlusion status is good when the impedance values recorded by the electrode initially decrease and then plateau.

A system for predicting lesion quality may include a treatment device including an occlusion element and an electrode distal to the occlusion element, the treatment device injecting an impedance-modifying agent into a pulmonary vein and a processor in communication with and receiving impedance data from the electrode, the processor programmed to: calculate a rate of impedance change over time after the impedance-modifying agent is injected into the pulmonary vein; determine a pulmonary vein occlusion status based at least in part on the rate of impedance change; and predict a lesion quality, the lesion quality being based at least in part on the pulmonary vein occlusion status. The impedance-modifying agent may increase impedance of a fluid within the pulmonary vein. For example, the processor may be programmed to determine the occlusion status is poor when the impedance values recorded by the electrode initially increase and then decrease over time, and the processor may be programmed to determine the occlusion status is good when the impedance values recorded by the electrode initially increase and then plateau. Alternatively, the impedance-modifying agent may decrease impedance of a fluid within the pulmonary vein. For example, the processor may be programmed to determine the occlusion status is poor when the impedance values recorded by the electrode initially decrease and then increase over time, and the processor may be programmed to determine the occlusion status is good when the impedance values recorded by the electrode initially decrease and then plateau.

A method for predicting lesion quality may include: injecting an impedance-modifying agent into a pulmonary vein from a medical device, the medical device including an occlusion element at least partially occluding the pulmonary vein and a distal electrode positioned within the pulmonary vein; recording a plurality of impedance values by the electrode within the pulmonary vein over a period of time after injection of the impedance-modifying agent into the pulmonary vein, the impedance-modifying agent one of increasing impedance within the pulmonary vein and decreasing impedance within the pulmonary vein; calculating a change in impedance values over the period of time; determining a pulmonary vein occlusion status based at least in part on the change in impedance values over the period of time, the pulmonary vein occlusion status being one of: complete occlusion when the impedance-modifying agent increases impedance within the pulmonary vein and the impedance values initially increase and then plateau; incomplete occlusion when the impedance-modifying agent increases impedance within the pulmonary vein and the impedance values initially increase and then decrease; complete occlusion when the impedance-modifying agent decreases impedance within the pulmonary vein and the impedance values initially decrease and then plateau; and incomplete occlusion when the impedance-modifying agent decreases impedance within the pulmonary vein and the impedance values initially decrease and then increase. The method may further include assessing the quality of an occlusion of the pulmonary vein by the medical device based on the determined pulmonary vein occlusion status; and at least one of: repositioning the medical device when the pulmonary vein occlusion status is determined to be incomplete occlusion; and ablating tissue surrounding the pulmonary vein with the occlusion element when the pulmonary vein occlusion status is determined to be complete occlusion.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
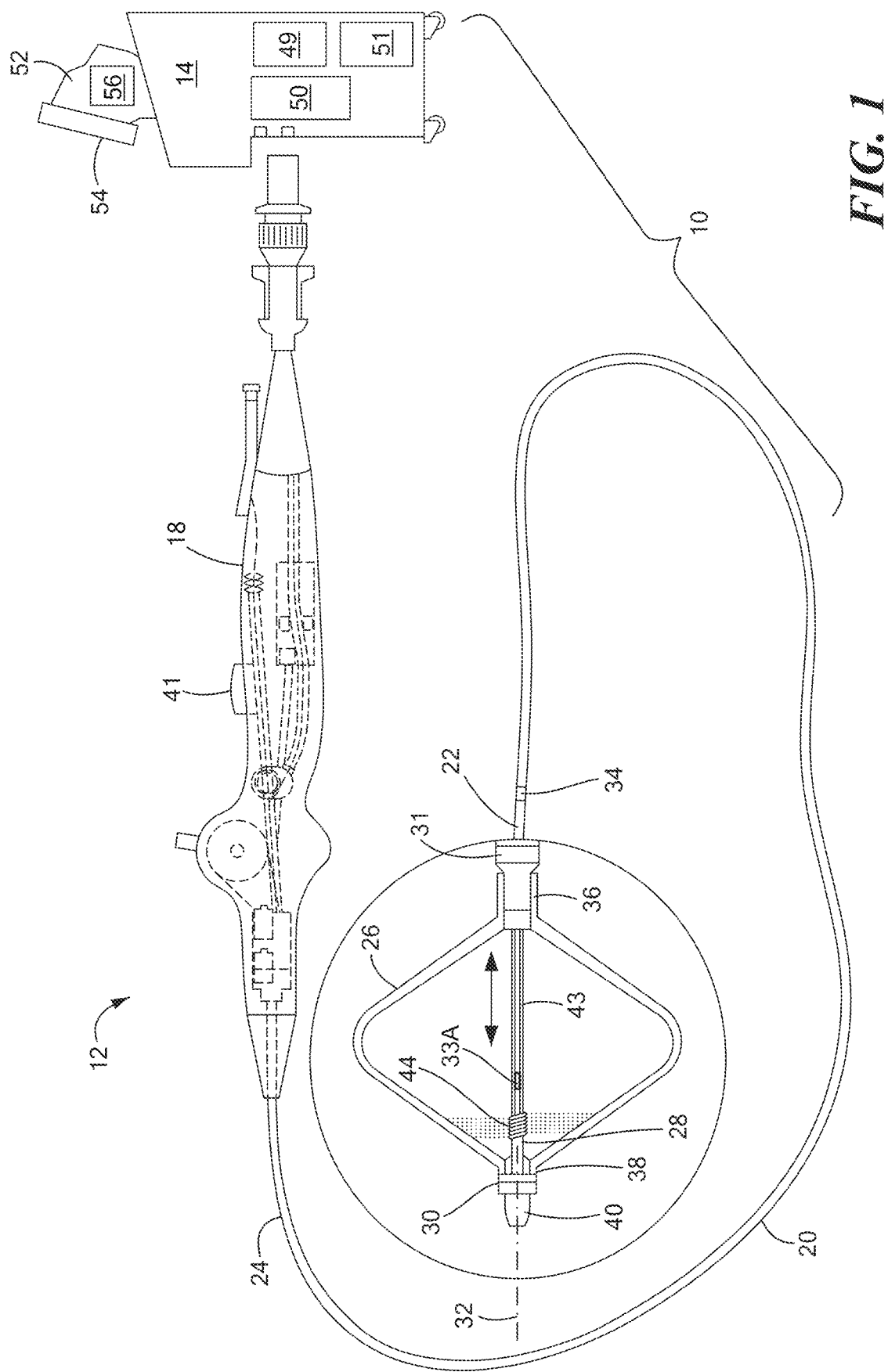
FIG. 1 shows an exemplary system for the assessment of pulmonary vein occlusion.
Figure 2:
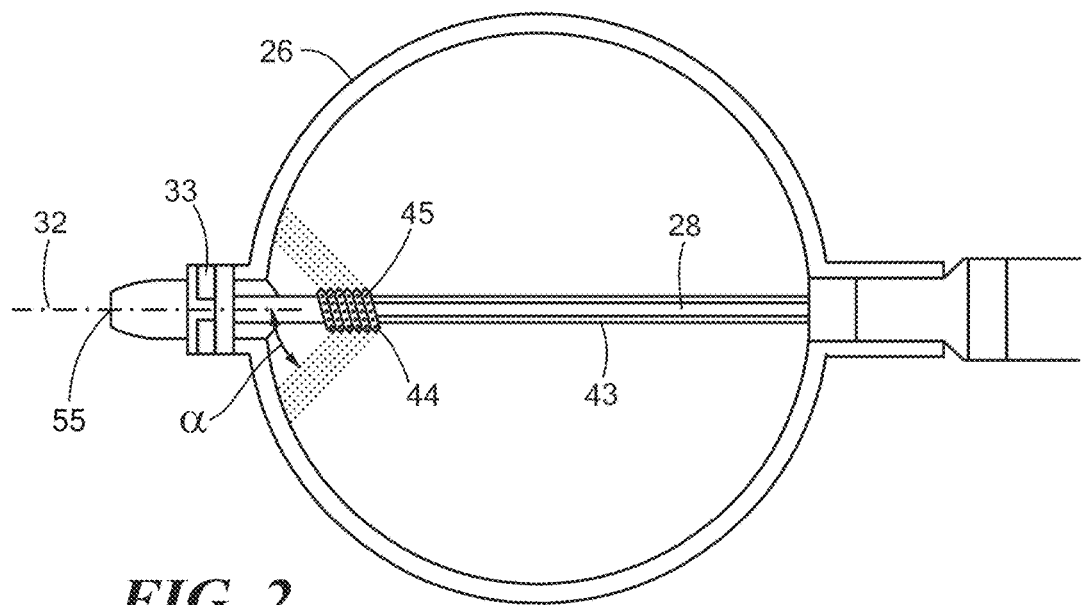
FIG. 2 shows a close-up view of a distal end of a medical device of the system in FIG. 1.

Referring now to FIGS. 1 and 2, an exemplary system for the assessment of pulmonary vein occlusion is shown. The system 10 may generally include a treatment device 12, such as a cryotreatment catheter, for thermally treating an area of tissue and a console 14 that houses various system 10 controls. The system 10 may be adapted for a cryotreatment procedure, such as cryoablation. The system 10 may additionally be adapted for radiofrequency (RF) ablation and/or phased RF ablation, ultrasound ablation, laser ablation, microwave ablation, hot balloon ablation, or other ablation methods or combinations thereof. The system 10 may also include a mapping catheter 16 for sensing and recording electrical signals from tissue (for example, cardiac tissue and/or tissue within a pulmonary vein).

Figure 3:
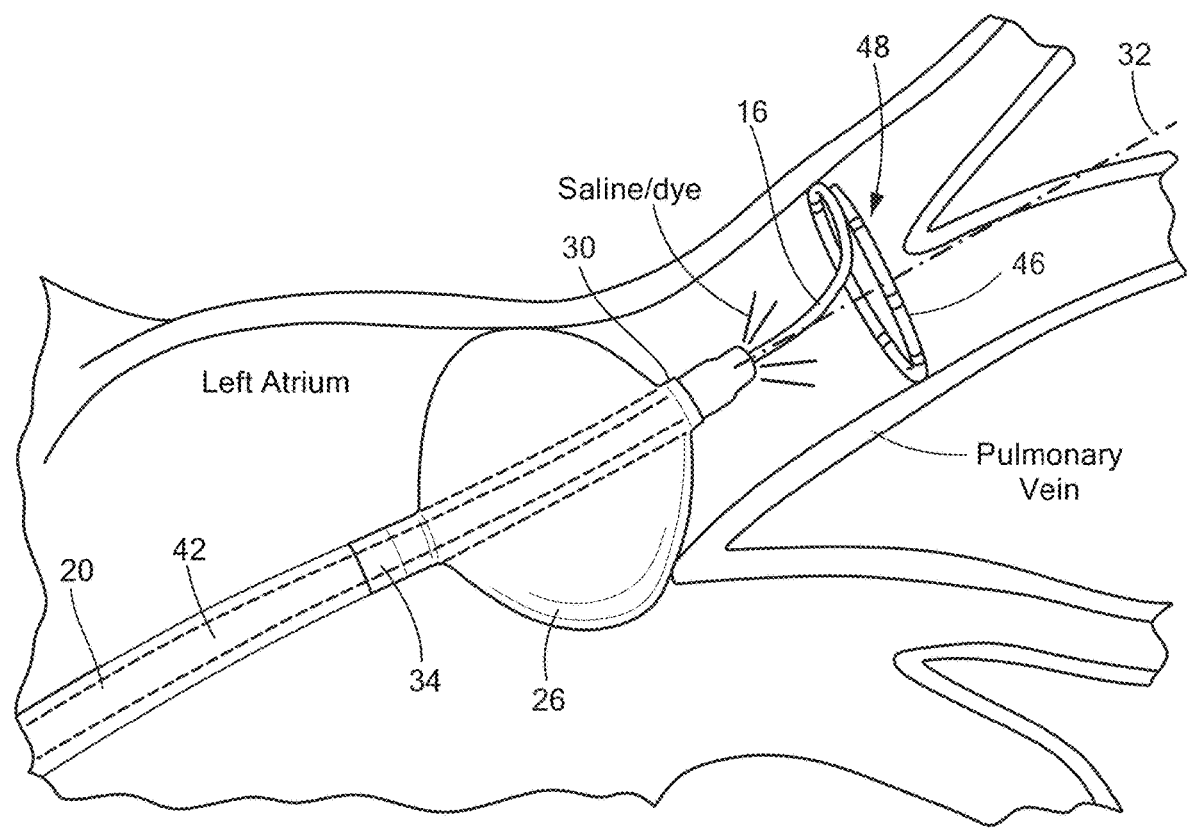
FIG. 3 shows an exemplary placement of the medical device of FIG. 2 proximate a pulmonary vein.

The treatment catheter 12 may generally include a handle 18, an elongate body 20 having a distal portion 22 and a proximal portion 24, one or more treatment elements 26, a shaft 28, an electrode 30 distal to the one or more treatment elements 26, and a longitudinal axis 32. The electrode 30 may be configured to measure both impedance and temperature. As a non-limiting example, the electrode 30 may be a 0.5 mm ring thermocouple electrode that functions as a thermocouple for recording temperature data and an electrode for delivering energy and/or recording impedance and/or other mapping data. Alternatively, the electrode 30 may measure impedance only and the treatment catheter 12 may additionally include one or more thermocouples or other temperature sensors 33. For example, the treatment catheter 12 may include one or more thermocouples 33 proximate (either distal to or proximal to) the electrode 30 (for example, as shown in FIG. 2). In either configuration, the treatment catheter 12 may also include a thermocouple or other temperature sensor 33A within the treatment element 26. Further, the treatment catheter 12 may include a reference electrode 34. The treatment element 26 may be a balloon, as shown in FIGS. 1-3, and may also function as an occlusion element. The balloon 26 may be coupled to the distal portion 22 of the elongate body 20 of the treatment catheter 12. For example, the balloon 26 may define a proximal portion or neck 36 that is affixed to or coupled to the distal portion 22 of the elongate body 20, and may further define a distal portion or neck 38 that is affixed to or coupled to the shaft 28 (such as the distal portion 40 of the shaft 28). The electrode 30 and/or one or more thermocouples 33 may be positioned just distal to the distal neck 38 of the balloon 26. However, it will be understood that the balloon 26 may be coupled, affixed, disposed on, integrated with, or otherwise attached to the elongate body 20 and/or the shaft 28. Additionally, multiple balloons may be used, such as when the balloon 26 is disposed within or without a second balloon (not shown). The shaft 28 may lie along the longitudinal axis 32 and be longitudinally movable within the elongate body 20. In this manner, longitudinal movement of the shaft 28 will affect the shape of the balloon 26. The proximal portion of the shaft 28 may be in mechanical communication with one or more steering mechanisms 41 in the handle 18 of the treatment catheter 12, such that the shaft 28 may be longitudinally extended or retracted using one or more steering mechanisms 41, such as knobs, levers, wheels, pull cords, and the like. The shaft 28 may include a central lumen 42 and an opening in the distal end of the shaft for delivering fluid, such as a mixture of a contrast medium and an impedance-modifying agent, into the patient's body (for example, the pulmonary vein).

In addition to the shaft 28, the treatment catheter 12 may include one or more lumens, such as a fluid injection lumen 43 and a fluid recovery lumen, for circulating coolant through from a fluid reservoir (which may be part of, disposed within, and/or in communication with the console 14) through the elongate body and to the balloon 26, and for recovering expended coolant from the balloon 26 and collecting the expended coolant within a fluid reservoir or venting to the atmosphere. Further, the treatment catheter 12 may include a fluid delivery element 44 that is in fluid communication with the fluid injection lumen 43. As a non-limiting example, the fluid delivery element 44 may be wound about at least a portion of the shaft 28 within the balloon 26, as shown in FIG. 1. The fluid delivery element 44 may be configured to direct a spray of coolant toward the distal portion of the balloon 26. The fluid delivery element 44 may direct coolant in a direction that is substantially orthogonal (that is, approximately 90°) (as shown in FIG. 1) to the longitudinal axis 32 or in a direction that is at an angle that is less than 90° to the longitudinal axis 32. For example, the fluid delivery element 44 may include a plurality of outlet ports 45 that are configured to deliver fluid at an angle α from the longitudinal axis 32 of the device, such as at an angle α of between approximately 30° and approximately 45° (±5°) (as shown in FIG. 2). However, it will be understood that the fluid delivery element 44 may have any configuration that is suitable for directing fluid toward the distal portion of the balloon 26. If the treatment catheter 12 includes thermoelectric cooling elements or electrodes capable of transmitting radiofrequency (RF), ultrasound, microwave, electroporation energy, or the like, the elongate body 20 may include a lumen in electrical communication with an energy generator (which may be part of, disposed within, and/or in communication with the console 14).

The mapping catheter 16 may be passable (longitudinally movable) through the shaft 28. The mapping catheter 16 may include one or more pairs of mapping elements 46, such as electrodes capable of sensing and recording electrograms from cardiac tissue. The one or more pairs of mapping elements 46 may be composed of metal or other electrically conductive material and may be affixed on an outer surface of the mapping catheter 16, integrated and flush with the body of the mapping catheter 16 (such that the mapping catheter has a smooth outer surface), may be areas of exposed electrically conductive material (for example, where an outer insulative layer has been removed), or may be otherwise affixed, coupled to, or integrated with the mapping catheter 16. The mapping catheter 16 may be in deformable and/or steerable using one or more steering mechanisms 41 into a variety of configurations. For example, the distal of the mapping catheter 16 may be deformable into a lasso-type configuration, such that the loop portion 48 and mapping elements 46 may be in contact with at least a portion of an inner circumference of a PV.

The console 14 may be in electrical and fluid communication with the treatment catheter 12 and the mapping catheter 16, and may include one or more fluid (for example, cryotreatment coolant) reservoirs, including an impedance-modifying agent reservoir 49, one or more coolant recovery and/or source reservoirs 50, energy generators 51, and computers 52 with displays 54, and may further include various other displays, screens, user input controls, keyboards, buttons, valves, conduits, connectors, power sources, processors, and computers for adjusting and monitoring system 10 parameters. The one or more coolant recovery and/or source reservoirs 50 may be in fluid communication with the balloon 26 and the impedance-modifying agent reservoir 49 may be in fluid communication with the central lumen 42 and distal opening 55 of the shaft 28. As used herein, the term "computer" may refer to any programmable data-processing unit, including a smart phone, dedicated internal circuitry, user control device, or the like. The computer 52 may include one or more processors 56 that are in electrical communication with the one or more pairs of mapping elements 46, the electrode 30, the one or more thermocouples 33, 33A, the one or more treatment elements 26, and/or one or more valves and programmable to execute an algorithm for locating one or more optimal treatment areas, for controlling the temperature of the one or more treatment elements 26, for generating one or more displays or alerts to notify the user of various system criteria or determinations, and/or for predicting temperature within target tissue based at least in part on signals from the electrode 30 and/or one or more other temperature sensors 33, 33A. As a non-limiting embodiment, the proximal portion of the mapping catheter 16 may include an electrical connection that is mateable to at least a portion of the console (for example, with the electrophysiology recording equipment) and in electrical communication with the one or more processors 56. Additionally, the electrode 30 may be in electrical communication with an energy generator 51 for the application of energy to the electrode 30 for sensing impedance and, optionally, for mapping cardiac electrograms from adjacent tissue and/or thermally treating tissue. Furthermore, electrodes 30 and 34 may be used for 3D navigation of the treatment catheter 12 within the atrial chamber and positioning the treatment catheter 12 within, for example, a pulmonary vein. This may allow the operator to avoid placing the one or more treatment elements 26 too deep within the pulmonary vein, and may enable the operator to avoid extracardiac tissues and again navigate the one or more treatment elements 26 into the pulmonary vein if repeated ablation is needed. Additionally, marking the position of the one or more treatment elements 26 may allow the operator to mark the ablated pulmonary veins if multiple pulmonary vein branches and common ostium is present.

The console 14 may also include one or more valves that are in electrical and/or mechanical communication with, and controllable by, the console 14. For example, the computer 52 and/or one or more processors 56 may be programmable to control various system components, such as the one or more valves, to operate according to a duty cycle that includes opening and closing the one or more valves to regulate the flow of coolant through the system 10 and the treatment catheter 12, and to thereby regulate the temperature of the treatment element 26 (for example, the balloon 26). The duty cycle may be programmable by the user and/or may be automatically set by the console 14 according to a predicted tissue temperature based at least in part on signals from the electrode 30, mapping elements 46, and/or temperature sensors 33, 33A.

Referring now to FIG. 2, a close-up view of the distal portion of a first embodiment of the balloon catheter is shown. As shown and described in FIG. 1, the treatment catheter 12 may include a distal electrode 30. The treatment catheter 12 may further include a reference electrode 34 and one or more thermocouples or other temperature sensors 33 if the electrode 30 is not configured to measure temperature. The electrodes 30 and 34 may be composed of an electrically conductive material suitable for sensing impedance and, optionally, temperature. As shown in FIGS. 1 and 2, the electrode 30 (and a thermocouple or temperature sensor 33, if included in the device) may be located distal to the balloon 26. The electrode 30 may be coupled to, affixed to, disposed about, integrated with, or otherwise located on a distal portion of the treatment catheter 12. The electrode 30 and/or one or more thermocouples 33 may be located immediately distal to the balloon 26, such as on the shaft distal portion 40. For example, the electrode 30 may be adjacent to or abut the distal end of the balloon 26. The reference electrode 34 may be located proximal to the balloon 26, such as on the elongate body distal portion 22. As a non-limiting example, the balloon 26 may have a diameter of approximately 23 mm to approximately 28 mm.

Referring now to FIG. 3, a treatment catheter is shown positioned proximate a pulmonary vein ostium for a pulmonary vein ablation procedure (which may also be referred to as a pulmonary vein isolation (PVI) procedure). As used herein, the term "PV tissue" or "pulmonary vein tissue" may include tissue of the PV ostium, the PV antrum, LA wall tissue, and/or tissue at the junction between the LA and PV, and is not limited to tissue within the PV. In fact, ablation of tissue within the PV may be undesirable. The inflated balloon 26 may be positioned at the pulmonary vein (PV) ostium to occlude the PV, or block the flow of blood from the PV into the left atrium (LA) of the heart. Occlusion of the PV not only serves to position the balloon 26 to create a circumferential lesion around the PV ostium, but also prevents warm blood from flowing over the portions of the balloon 26 that are in contact with the target tissue, thereby enhancing the ability of the balloon 26 to reach sufficiently cold temperatures for creating permanent, and circumferential, cryoablation lesions on or in the target tissue. If the PV is not completely occluded, blood flow past the balloon 26 may have the effect of raising the temperature of the balloon 26, possibly resulting in the formation of reversible lesions on or in the target tissue. The blocked blood within the PV may be referred to as "stagnant" blood, whereas the blood within the LA may be referred to as "flowing" blood, as blood may still enter the LA from the other three PVs that are not being occluded by the treatment catheter 12.

As shown in FIG. 3, the balloon 26 may be positioned at the PV ostium such that the shaft distal portion 40, including the electrode 30 and/or one or more thermocouples 33, is disposed within the PV, within the stagnant blood. An injection of an impedance-modifying agent only or a mixture of a biocompatible contrast medium and an impedance-modifying agent may be introduced into the PV at a fixed rate, volume, and temperature. As a non-limiting example, the contrast medium/agent mixture may be expelled in an amount of approximately eight cc and at a pressure of approximately 125±12 PSI.

As noted above, an agent may be used that alters the conductivity of the blood within the pulmonary vein when injected from the treatment catheter 12 into the pulmonary vein and mixes with the blood. For example, the agent may be, for example, sterile water, deionized water, iodine solution (diluted in saline 50%), distilled water, or hypertonic saline with typical boluses of up to 10 cc injected from the device. Although the agent may be injected in a fluid mixture referred to herein as a "contrast medium/agent mixture," it will be understood that the agent alone may be used when mixed with contrast medium. However, it will be understood that any agent or contrast medium/agent mixture will be injected into the patient's body in small enough amounts to avoid interfering with the blood's normal ionic balance and negatively affecting body function. Further, the agent may be used alone without contrast medium if the patient is intolerant to contrast medium, such as due to an allergy or kidney problems, or if it is desired to reduce or eliminate the use of fluoroscopy.

Figure 4A:
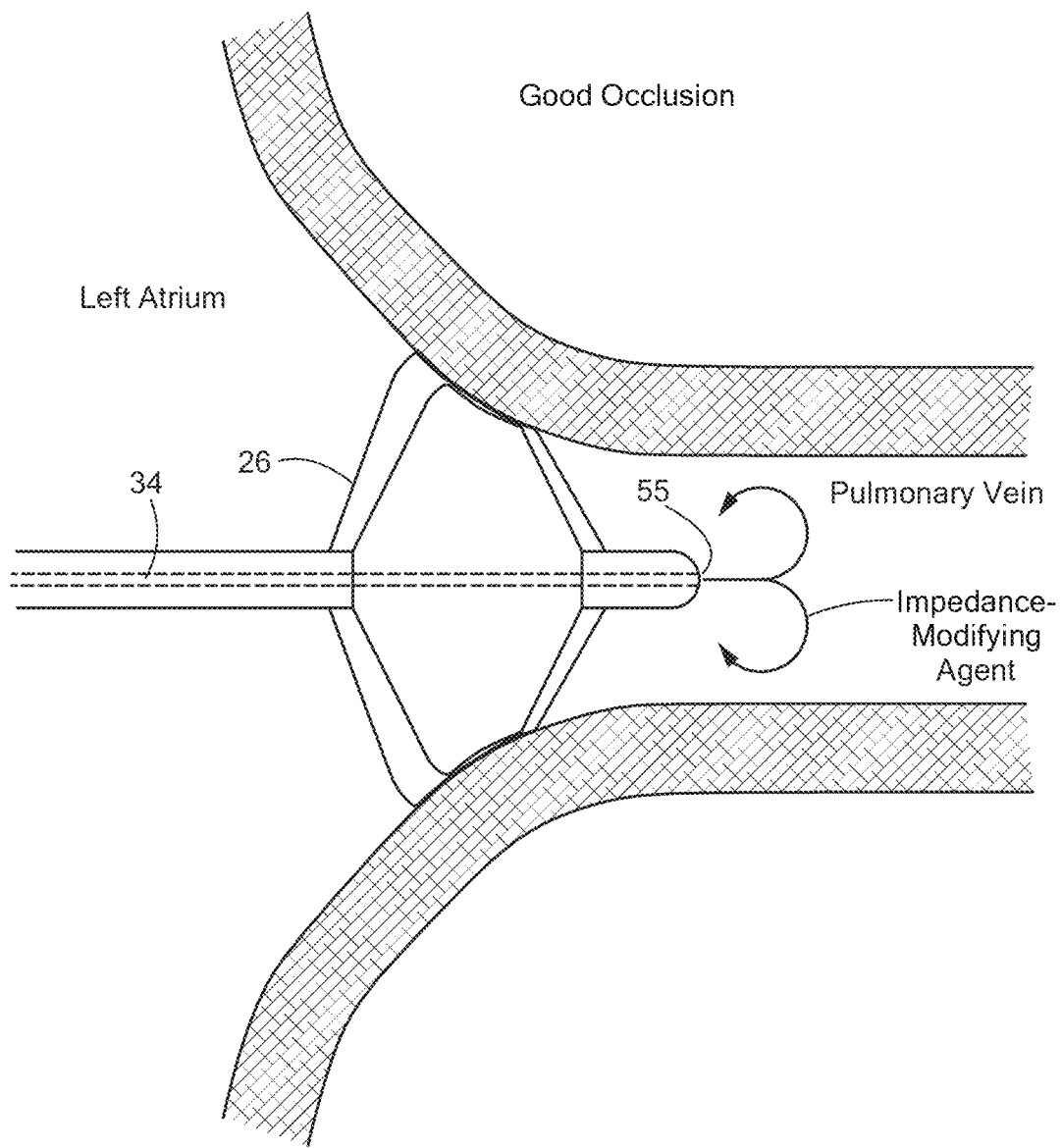
FIG. 4A shows a distal portion of a medical device completely occluding a pulmonary vein.
Figure 4B:
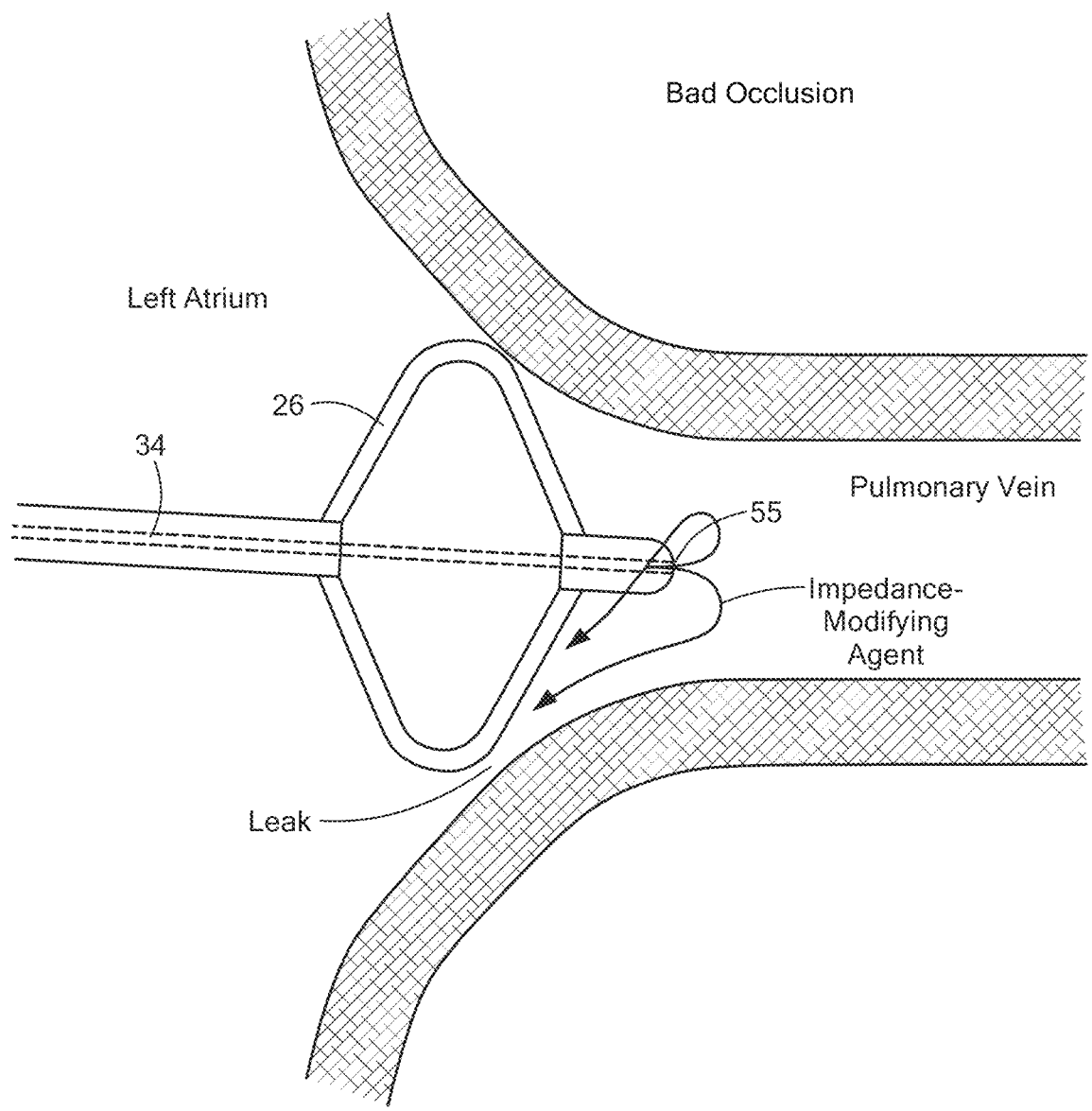
FIG. 4B shows a distal portion of a medical device partially occluding a pulmonary vein.
Figure 5A:
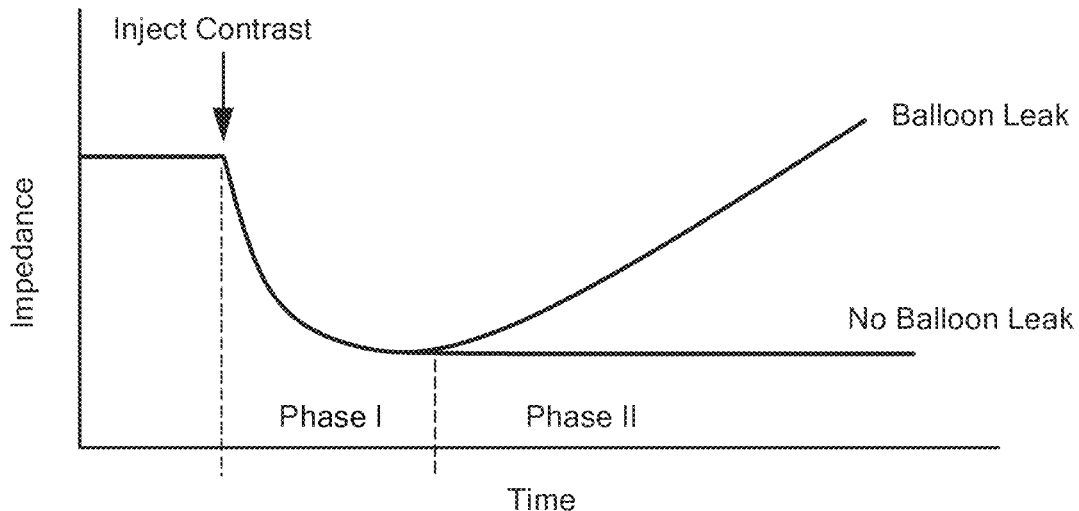
FIG. 5A shows a graphical representation of changes in impedance when a contrast with impedance-increasing agent is injected into a pulmonary vein.

The agent may adjust the conductivity (and therefore impedance) of blood by either increasing blood conductivity (for example, if a hypertonic solution is used) or decreasing blood conductivity (for example, if distilled water, sterile water, or deionized water is used). An agent that increases blood conductivity may lead to a decrease in impedance within the PV as measured by the treatment catheter 12 as the contrast medium/agent mixture is injected into the PV (for example, from the opening in the distal end of the shaft 28). If the balloon 26 is completely occluding the PV (as shown in FIG. 4A), the local impedance within the PV may remain low for a longer period. If, on the other hand, the balloon 26 is partially or incompletely occluding the PV (as shown in FIG. 4B), the contrast medium/agent mixture may leak past the balloon 26 out of the PV and into the left atrium. In that case, a decrease in local impedance will not be as significant and will remain for a shorter period of time until all of the contrast medium/agent mixture has flowed from the PV into the left atrium. These trends in impedance value change are shown in FIG. 5A. In FIG. 5A, a mixture of contrast medium and an agent that increases conductivity may be injected into the pulmonary vein and impedance values recorded by the electrode 30. During Phase I, the impedance will initially decrease. If the PV is completely occluded, the impedance will remain low during Phase II (that is, the values plateau). If, on the other hand, the PV is less than completely occluded, the impedance will increase during Phase II.

Figure 5B:
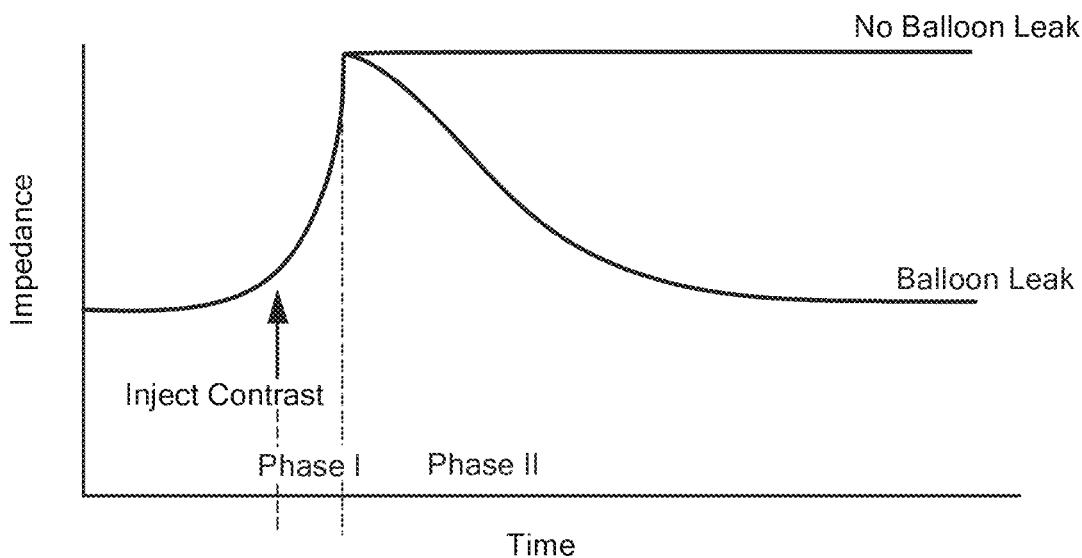
FIG. 5B shows a graphical representation of changes in impedance when a contrast with impedance-decreasing agent is injected into a pulmonary vein.

Conversely, an agent that decreases blood conductivity may lead to an increase in impedance within the PV as measured by the treatment catheter 12 as the contrast medium/agent mixture is injected into the PV (for example, from the opening in the distal end of the shaft 28). A small leak around the balloon 26 may not produce as great an impedance change (that is, it may produce a change having a lower peak for a shorter period of time), whereas complete occlusion (an absence of a leak) may result in impedance within the PV may produce a change having a higher peak for a longer period of time (that is, an impedance curve having a bigger crest and a larger surface area under the curve). These trends in impedance value change are shown in FIG. 5B. In FIG. 5B, a mixture of contrast medium and an agent that decreases conductivity may be injected into the pulmonary vein and impedance values recorded by the electrode 30. During Phase I, the impedance will initially increase. If the PV is completely occluded, the impedance will remain high during Phase II (that is, the values plateau). If, on the other hand, the PV is less than completely occluded, the impedance will decrease more rapidly during Phase II in proportion to the leak rate.

Figure 6A:
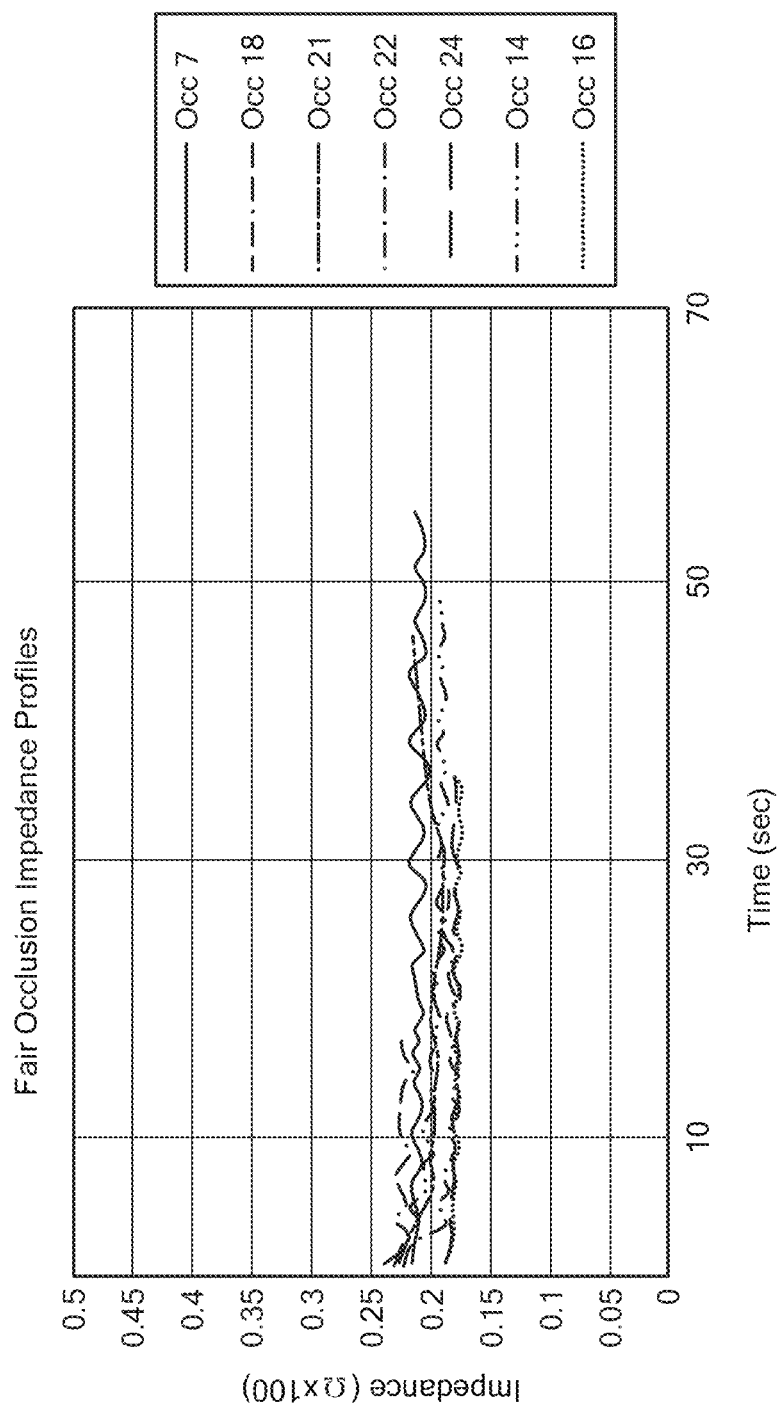
FIGS. 6A-6C show exemplary charts of data for the assessment of pulmonary vein occlusion based on impedance when an impedance-decreasing agent is injected into a pulmonary vein.
Figure 6B:
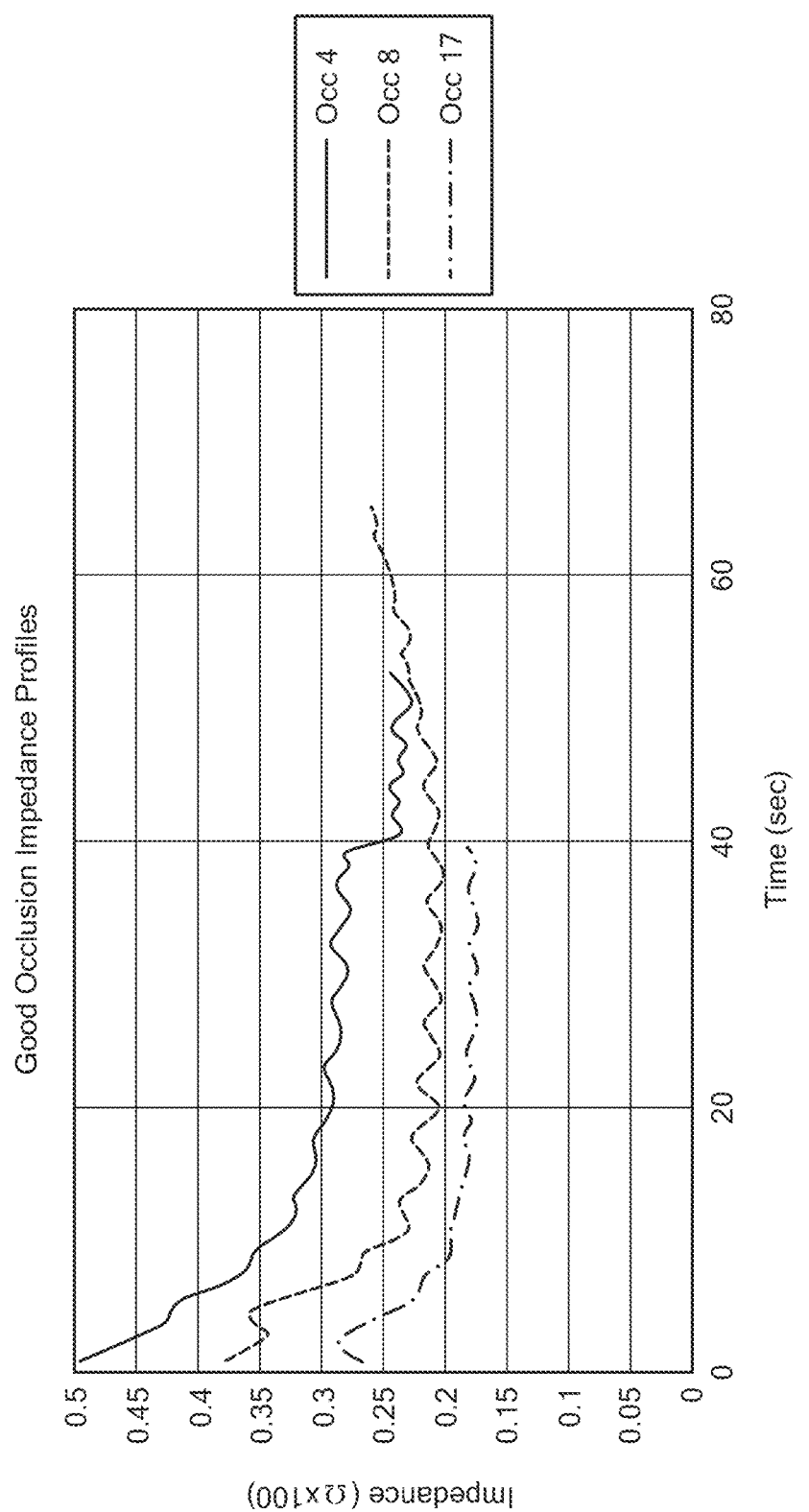
Figure 6C:
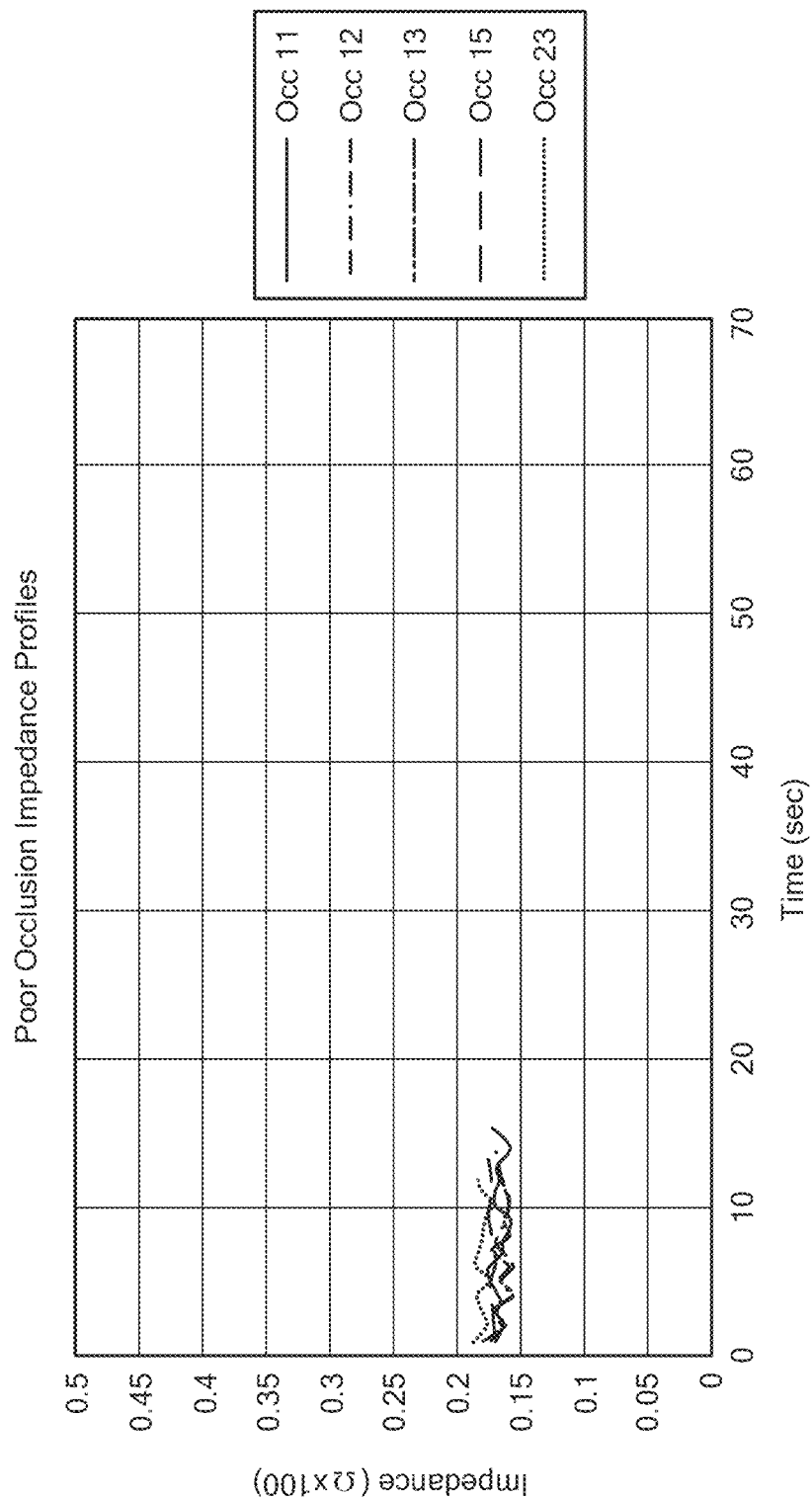

FIGS. 6A-6C show impedance curves for fair occlusion, good occlusion, and poor occlusion, respectively, using only sterile water, which decreases blood conductivity. FIGS. 6A-6C show impedance curves over Phase II, or impedance changes after the injection of the agent. Although the data shown in FIGS. 6A-6C was obtained by injecting agent only (sterile water), it will be understood that a contrast medium/agent mixture may be used instead. In FIG. 6A, the presence of a leak is indicated by the low impedance values. In FIG. 6B, good occlusion is indicated by the relatively higher impedance values.

Continuous impedance and temperature measurements may be taken during device placement and ablation by the electrode 30 and/or mapping elements 46 of the mapping catheter 16 and the measurements may be used to determine whether the PV is completely occluded. As discussed above, changes in impedance after injection of a contrast medium/agent mixture into the PV may be monitored to evaluate PV occlusion quality. Further, if changes in impedance indicate that the PV is less than completely occluded, the rate of impedance change (that is, as the contrast medium/agent mixture leaks into the left atrium) may be correlated to the degree of occlusion. For example, a higher peak and small rate of change may indicate that a small leak is present, whereas a smaller peak and greater rate of change may indicate that a larger leak is present. Complete occlusion may suggest that a permanent lesion will be formed as a result of the ablation procedure.

If impedance measurements indicate that the PV is not permanently ablated and/or less than fully occluded, the treatment catheter 12 may be repositioned until complete PV occlusion is indicated by evaluation of the impedance temperature measurements. For example, the one or more processors 56 of the console computer 52 may be programmed to receive and process data from the one or more electrodes and/or thermocouples, and to generate an alert to the user indicating that the device should be repositioned to achieve complete PV occlusion or that the device is already optimally positioned.

In addition to impedance measurements, a visual evaluation may also be used to assess PV occlusion. For example, fluoroscopic imaging may be used to visually evaluate the time it takes for the contrast medium/agent mixture to dissipate from the area of the PV proximate the treatment catheter 12. Further, visual evaluation may be used in addition to temperature measurements. Generally, if the PV is completely occluded by the treatment element 26, it will take longer for the contrast medium/agent mixture (which may appear as being darker than the surrounding blood under fluoroscopic imaging) to dissipate from the area proximate the treatment catheter 12. In contrast, if PV occlusion is poor, the contrast medium/agent mixture may quickly dissipate with the normal direction of blood flow, such as from the pulmonary vein into the left atrium of the heart.

After PV occlusion assessment, which may be conducted prior to thermally treating target tissue, the balloon 26 may then be cooled to a temperature sufficient to ablate tissue and applied to the tissue surrounding the PV opening (for example, the PV ostium and/or the PV antrum). Once the balloon 26 has reached ablation temperature, the temperature sensed by the electrode 30 or the thermocouple positioned distal to the balloon 26 and within the PV and a temperature sensed within the balloon may be compared for each of the occlusion ratings (i.e. good occlusion, fair occlusion, and poor occlusion). The thermocouple or other temperature sensor 33A may be located within the balloon 26.

Figure 7A:
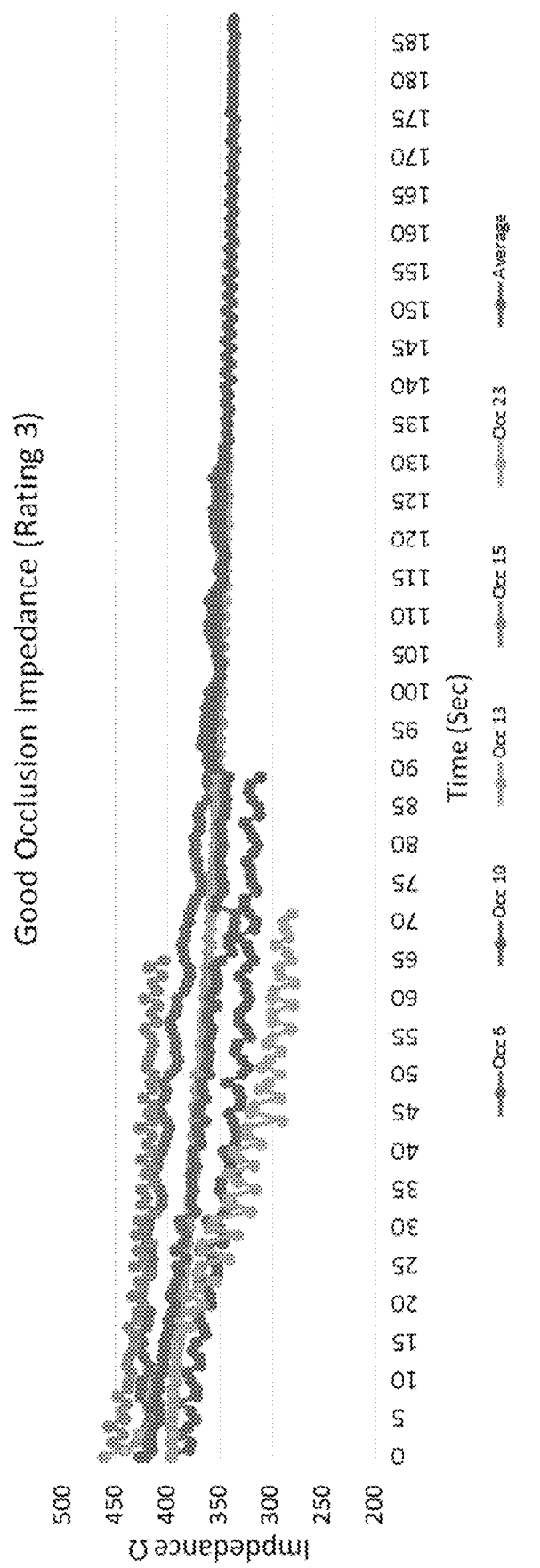
FIGS. 7A-7D show exemplary charts of data for the assessment of pulmonary vein occlusion based on impedance.
Figure 7B:
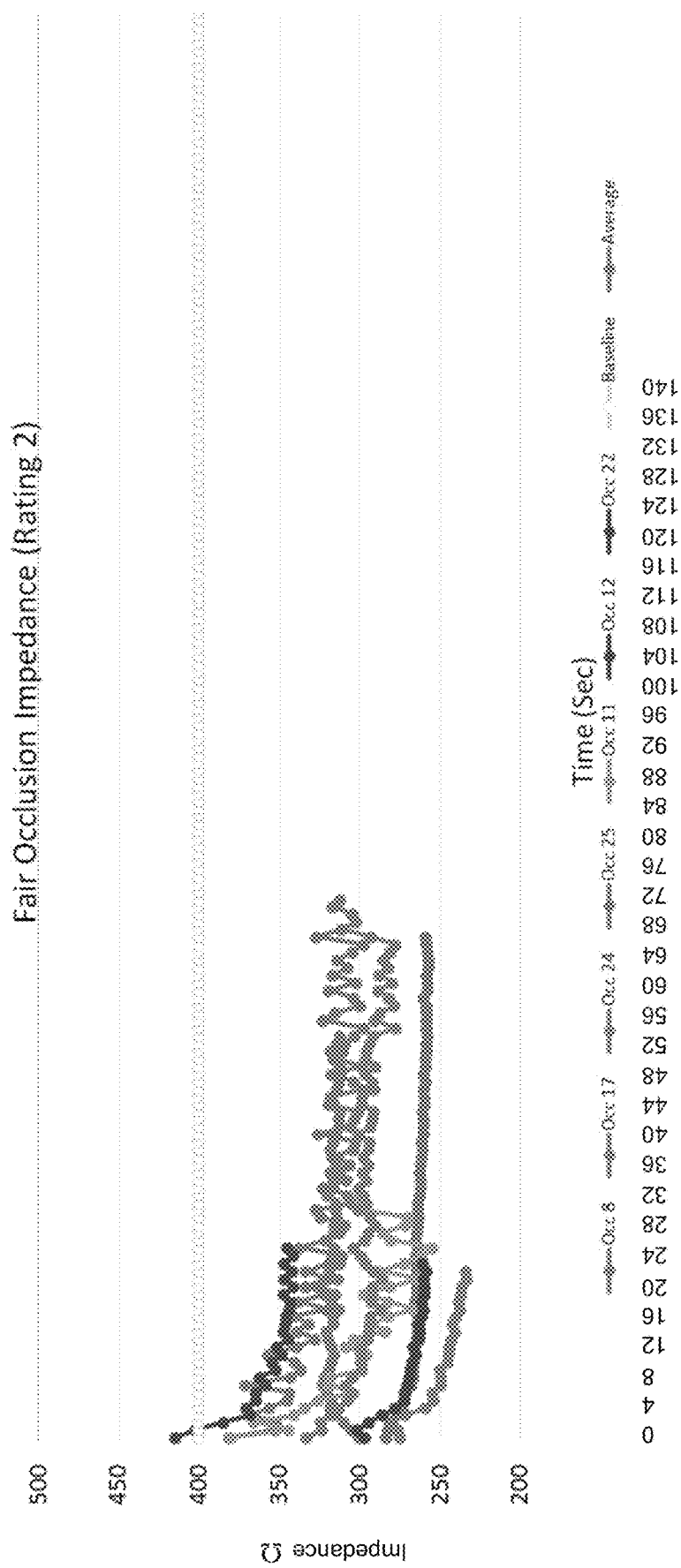
Figure 7C:
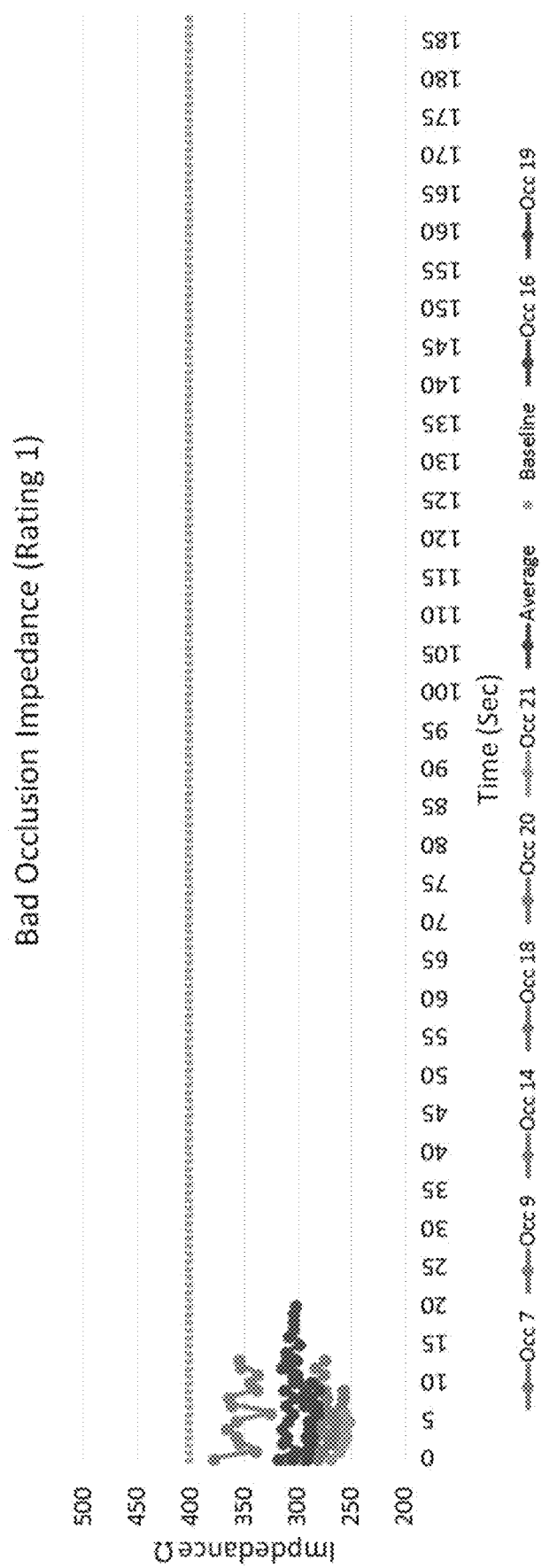
Figure 7D:
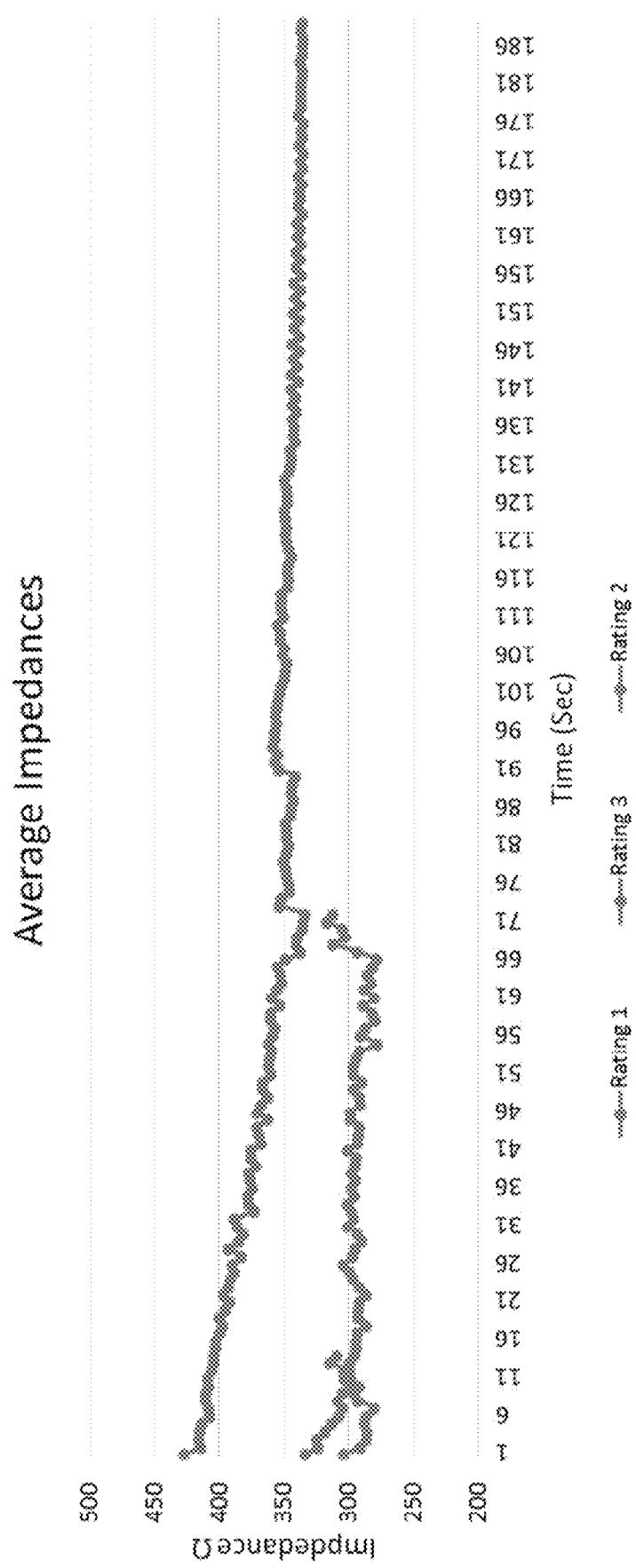

Similar to FIGS. 6A and 6B, FIGS. 7A-7D show assessment of PV occlusion based on impedance sensed by the distal electrode 30. FIG. 7A shows impedance curves over time for five discrete tests and an average impedance curve over time for an occlusion that is considered to be a good occlusion using a contrast medium/agent mixture that decreases conductivity (for example, a non-ionic contrast medium/saline mixture). FIGS. 7A-7D show impedance curves over Phase II, or impedance changes after the injection of the contrast medium/agent mixture. Although the data shown in FIGS. 7A-7D was obtained by injecting a contrast medium/agent mixture, it will be understood that only an agent may be used instead. FIG. 7B shows impedance curves over time for seven discrete tests, an average impedance curve over time, and a baseline impedance curve for an occlusion that is considered to be a fair occlusion. FIG. 7C shows impedance curves over time for eight discrete tests, an average impedance curve over time, and a baseline impedance curve for an occlusion that is considered to be a poor occlusion. FIG. 7D shows exemplary average impedance curves over time for each of occlusions that are considered to be good (referred to as "Rating 3" in FIG. 7D), fair (referred to as "Rating 2" in FIG. 7D), and poor (referred to as "Rating 1" in FIG. 7D) occlusions.

Figure 8A:
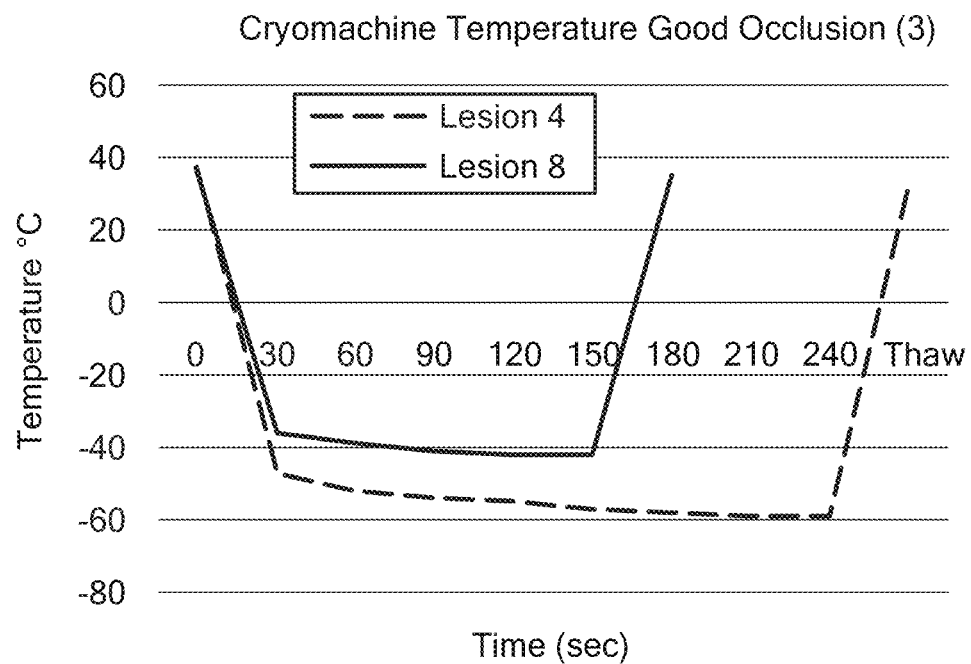
FIGS. 8A-8C show exemplary charts of data showing cryoablation quality based on a pre-assessed occlusion by temperature.
Figure 8B:
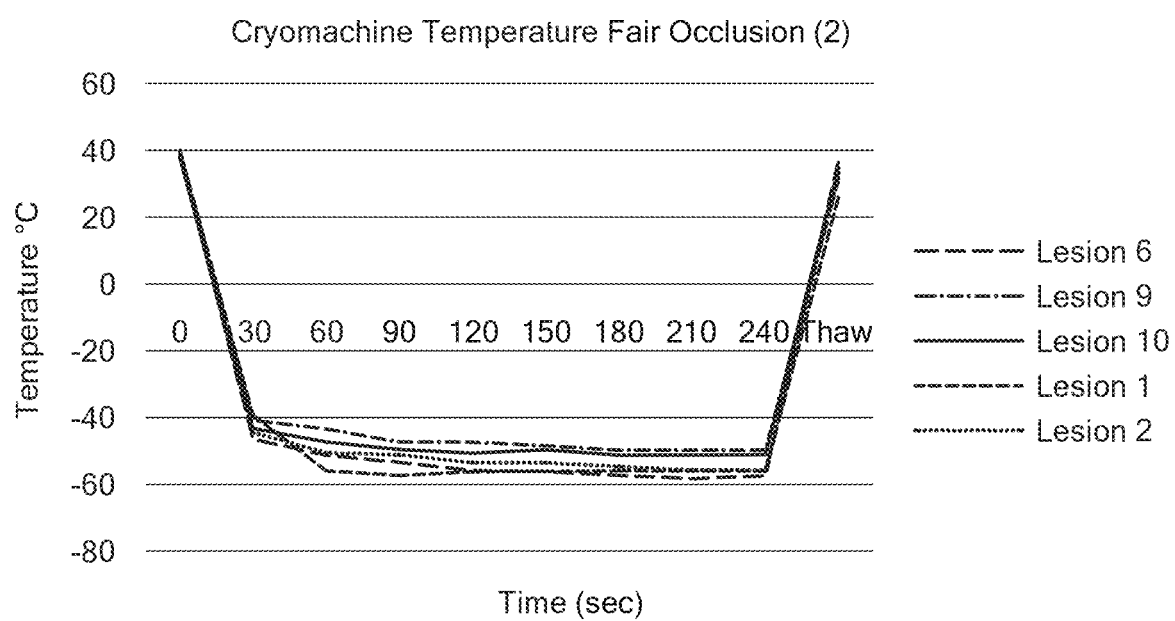
Figure 8C:
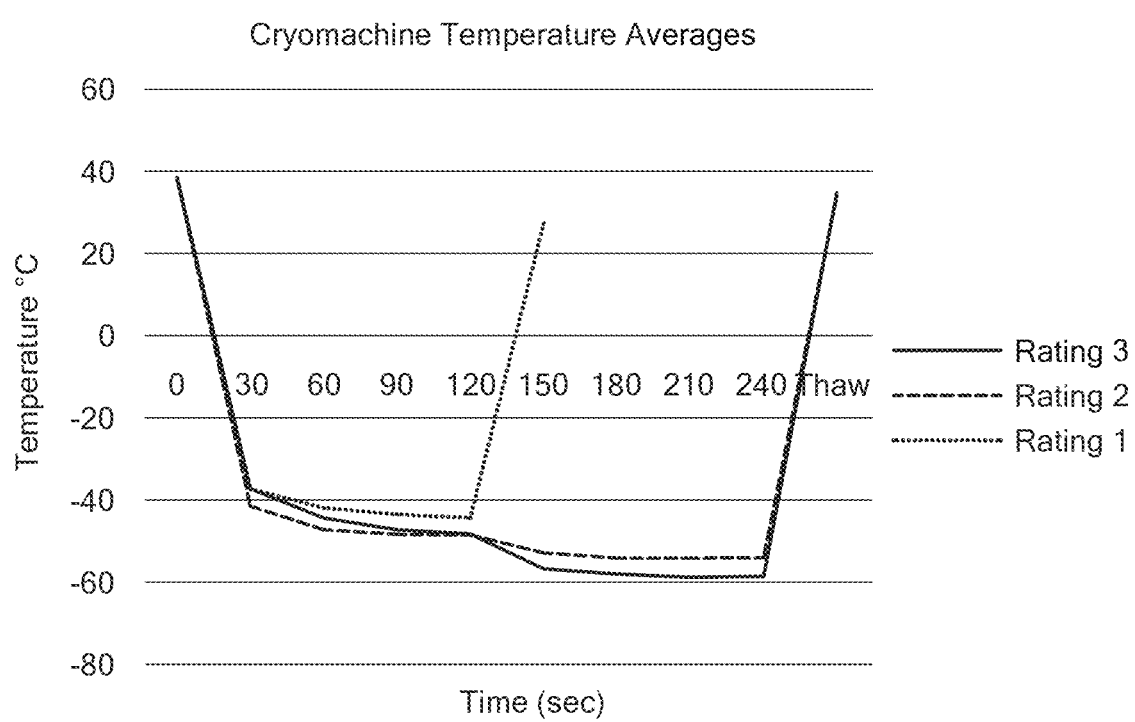

FIGS. 8A-8I show cryoablation quality based on a pre-assessed occlusion by temperature measurements. For example, FIG. 8A shows temperature curves over time as measured by a thermocouple 33A within the balloon 26 for two discrete tests, the data indicating that cryoablation quality is high as a result of what is considered to be a good occlusion. FIG. 8B temperature curves over time as measured by a thermocouple 33A within the balloon 26 for five discrete testes, the data indicating that the cryoablation quality is fair as a result of what is considered to be a fair occlusion. FIG. 8C shows exemplary average temperature curves over time as measured by a thermocouple 33A within the balloon 26 for each of occlusions that are considered to be good (referred to as "Rating 3" in FIG. 8C), fair (referred to as "Rating 2" in FIG. 8C), and poor (referred to as "Rating 1" in FIG. 8C). Temperature data Using data received by the electrodes 30 and, optionally, the one or more thermocouples 33, 33A, the occlusion can be qualified as good, fair, or poor by the one or more processors 56. For example, the one or more processors 56 may receive and process data from the treatment catheter 12 and the mapping device 16, and may use the data to calculate rates of impedance change over time ($\Delta I/\Delta t$) and determine or assign an occlusion status based on the impedance-modifying effects of the contrast medium/agent mixture or agent alone. That is, whether the agent (alone or mixed with a contrast medium) increases or decreases blood impedance will be considered by the one or more processors 56 in making an occlusion status determination, as discussed above. Additionally, the one or more processors 56 may use the occlusion status determination to predict lesion quality, based on the phenomenon that good occlusion will result in good lesion quality. The one or more processors 56 may further communicate determinations and/or the calculations to the user via the one or more displays 54. Additionally or alternatively, the system 10 may communicate results to the user via one or more visual or audio alerts. Occlusion assessment determinations may be displayed to the user graphically in a manner that is quickly understood. As a non-limiting example, a colored graphical element may be displayed, with the color green indicating good PV occlusion, the color yellow indicating fair PV occlusion, and the color red indicating poor PV occlusion.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims

What is claimed is:

1. A system for assessing occlusion, the system comprising:
   a treatment device including an expandable element, the expandable element comprising at least one electrode, wherein the at least one electrode includes at least one thermocouple electrode; and
   a console including:
   an energy generator, and
   a processor in electrical communication with the at least one electrode and the energy generator, the processor programmed to receive a signal that represents a temperature from the at least one thermocouple electrode, to calculate a change in the temperature over time, and to determine an occlusion status based upon the change in temperature.

2. The system of claim 1, wherein the processor is further programmed to predict the quality of a lesion created in tissue by the expandable element based upon a temperature status determination.

3. The system of claim 1, wherein a determination that the pulmonary vein is partially occluded includes at least one of assigning the occlusion a poor rating and assigning the occlusion a fair rating and a determination that the pulmonary vein is completely occluded includes assigning the occlusion a good rating.

4. The system of claim 3, wherein occlusion is assigned a good rating when the change in temperature values has a first value, occlusion is assigned a fair rating when the change in temperature values has a second value, and occlusion is assigned a poor rating when the change in temperature value has a third value.

5. The system of claim 1, wherein the at least one electrode is a 0.5 mm ring thermocouple electrode.

6. The system of claim 1, wherein the expandable element is a balloon.

7. The system of claim 1, wherein the processor is programmed to determine the occlusion status is good when the temperature values recorded by the electrode initially decrease at a first rate and continue to decrease at a second rate over a period of time, the first rate being faster than the second rate.

8. The system of claim 1, wherein the processor is programmed to determine the occlusion status is poor when the temperature values recorded by the electrode initially decrease and then plateaus for a period of time.

9. The system of claim 1, wherein the processor is programmed to determine a position of the expandable element relative to an area of tissue based on a temperature measurement received from the electrode.

10. The system of claim 9, wherein the area of tissue is an ostium of a pulmonary vein, the processor being further programmed to:
    receive temperature data from the electrode, the temperature data being recorded by the electrode before, during, and after a delivery energy to the electrode within the expandable element;
    calculate a temperature change over time; and
    determine an occlusion status of the ostium of the pulmonary vein by the treatment device based on the calculated temperature change over time.

11. The system of claim 10, wherein the temperature data is recoded by the processor continuously before, during, and after the delivery of an energy to the electrode within the expandable element.

12. The system of claim 1, wherein the treatment device further includes a shaft having a central lumen and a distal opening, the shaft being at least partially disposed within the expandable element, the central lumen and the distal opening being in communication with the energy generator.

13. The system of claim 1, wherein the processor is further programmed to receive a signal that represents an impedance from the at least one electrode, and wherein the processor is programmed to determine the occlusion status by determining the occlusion status based upon the impedance and the change in temperature.

14. A system for assessing occlusion, the system comprising:
    a treatment device including:
    an elongate body having a proximal portion, a distal portion, and a lumen therebetween;
    an expandable element coupled to the distal portion of the elongate body;
    the expandable element further including at least one electrode, wherein the at least one electrode includes at least one thermocouple electrode;

a shaft disposed within the lumen of the elongate body and having a fluid injection lumen, the expandable element being coupled to at least a portion of the shaft and the fluid injection lumen being disposed within the expandable element;

a fluid reservoir containing cryogenic fluid, the fluid reservoir being in fluid communication with the fluid injection lumen of the shaft; and a processor in electrical communication with the at least one electrode, the processor programmed to receive a signal that represents a temperature from the at least one thermocouple electrode, to calculate a change in the temperature over time based on the signal from the at least one thermocouple electrode, and to determine an occlusion status based upon the change in the temperature.

15. The system of claim 14, wherein the processor is programmed to determine the occlusion status is good when the temperature values recorded by the electrode initially decrease at a first rate and continue to decrease at a second rate over a period of time, the first rate being faster than the second rate.

16. The system of claim 14, wherein the processor is programmed to determine the occlusion status is poor when the temperature values recorded by the electrode initially decrease and then plateaus for a period of time.

17. The system of claim 14, wherein the processor is programmed to determine a position of the expandable element relative to an area of tissue based on a temperature measurement received from the electrode.

18. The system of claim 14, wherein the cryogenic fluid is cryotreatment coolant.

19. A method for predicting lesion quality, the method including:

injecting a cryogenic fluid into a medical device, the medical device including an expandable element at least partially occluding the pulmonary vein and a thermocouple electrode;

recording a plurality of temperature values based on signals received from the thermocouple electrode over a period of time after injection of the cryogenic fluid into the expandable element;

calculating a change in temperature values of the plurality of temperature values over the period of time;

comparing the change in temperature values over the period of time to a target change in temperature values over time;

determining a pulmonary vein occlusion status based at least in part on the change in temperature values over the period of time, the pulmonary vein occlusion status being one of complete occlusion and incomplete occlusion; and repositioning the medical device when the pulmonary vein occlusion status is determined to be incomplete occlusion.

20. The method of claim 19, further comprising:

determining the pulmonary vein occlusion status is complete occlusion when the temperature values recorded by the electrode initially decrease at a first rate and continue to decrease at a second rate over a period of time, the first rate being faster than the second rate; and determining the pulmonary vein occlusion status is incomplete occlusion when the temperature values recorded by the electrode initially decrease and then plateaus for a period of time.

* * * * *